United States Patent [19]

Floyd

[11] Patent Number: 4,568,489
[45] Date of Patent: Feb. 4, 1986

[54] N-ACYL-γ-GLUTAMYL IMINO AND AMINO ACIDS AND ESTERS

[75] Inventor: David Floyd, Pennington, N.J.

[73] Assignee: E. R. Squibb & Sons, Inc., Princeton, N.J.

[21] Appl. No.: 626,166

[22] Filed: Jun. 29, 1984

[51] Int. Cl.⁴ ............... C07C 103/52; C07D 217/00; C07D 491/00; C07D 209/42; C07D 209/44; C07D 207/00
[52] U.S. Cl. .................... 260/112.5 R; 548/533; 548/470; 548/492; 548/410; 548/491; 546/147
[58] Field of Search ............ 260/112.5 R; 548/533, 548/470, 410, 492; 546/147; 544/491

[56] References Cited

U.S. PATENT DOCUMENTS

| | | | |
|---|---|---|---|
| 2,581,814 | 1/1952 | Plentl | 260/112.5 R |
| 2,933,487 | 4/1960 | Amiard et al. | 260/112.5 R |
| 2,970,136 | 1/1961 | Amiard et al. | 260/112.5 R |
| 3,331,828 | 7/1967 | Inamine et al. | 260/112.5 R |
| 4,052,372 | 10/1977 | Finot et al. | 260/112.5 R |
| 4,052,511 | 10/1977 | Cushman et al. | 424/274 |
| 4,105,789 | 8/1978 | Ondetti et al. | 424/309 |

OTHER PUBLICATIONS

Ondetti et al., "The Use of an Active Site Model . . . ", Peptides, Proc. Fifth Amer. Peptide Symposium, 1977, pp. 576–578.

Primary Examiner—Delbert R. Phillips
Attorney, Agent, or Firm—Lawrence S. Levinson; Stephen B. Davis

[57] ABSTRACT

Compounds of the formula

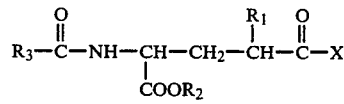

wherein X is various imino or amino acids or esters are disclosed. These compounds possess angiotensin converting enzyme inhibition activity and depending upon the definition of X also possess enkephalinase inhibition activity.

8 Claims, No Drawings

N-ACYL-γ-GLUTAMYL IMINO AND AMINO ACIDS AND ESTERS

BACKGROUND OF THE INVENTION

Cushman et al. in U.S. Pat. No. 4,052,511 disclose that various carboxyalkanoyl prolines, pipecolic acids, and azetidine-2-carboxylic acids possess angiotensin converting enzyme inhibition activity.

Ondetti et al. in U.S. Pat. No. 4,105,789 disclose that various carboxyalkanoyl amino acids possess angiotensin converting enzyme inhibition activity.

Ondetti et al. in an article entitled "The Use Of An Active Site Model In The Design Of Specific Inhibitors Of Angiotensin Converting Enzyme", Peptides-Proceedings Of The Fifth American Peptide Symposium (1977), discuss the in vitro angiotensin converting enzyme inhibition activity of various compounds including 1-(L-4-amino-4-carboxy-1-oxobutyl)-L-proline.

SUMMARY OF THE INVENTION

This invention is directed to new N-acyl-γ-glutamyl imino and amino acids and ester and pharmaceutically acceptable salts thereof of the formula $$R_3-\overset{O}{\overset{\|}{C}}-NH-\overset{*}{\underset{COOR_2}{CH}}-CH_2-\underset{R_1}{CH}-\overset{O}{\overset{\|}{C}}-X. \quad (I)$$

X is an amino or imino acid or ester of the formula

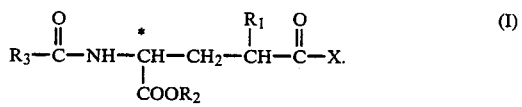

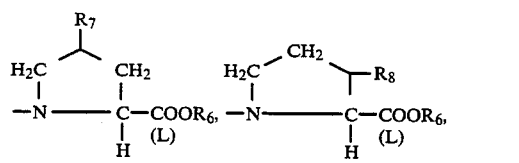

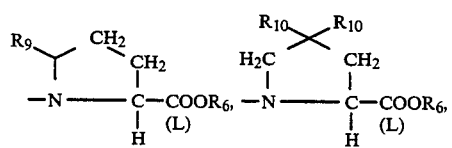

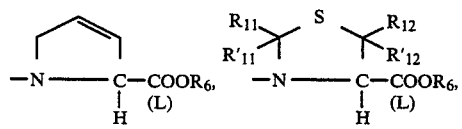

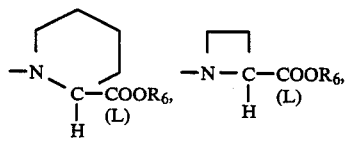

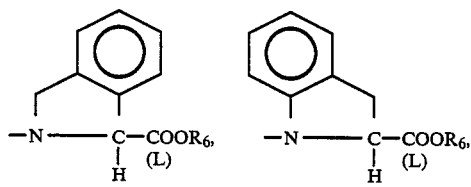

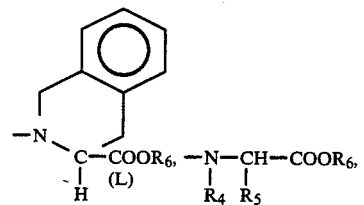

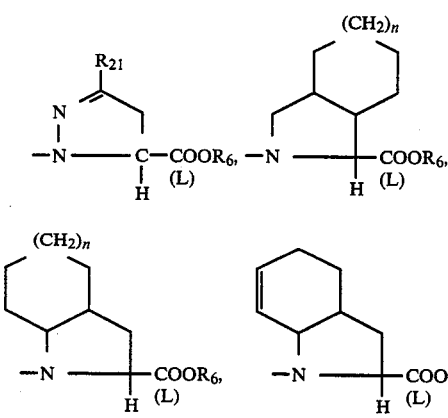

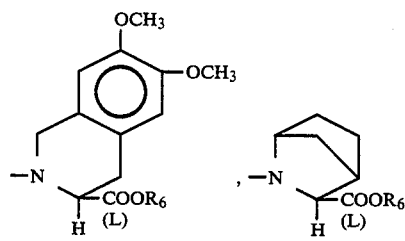

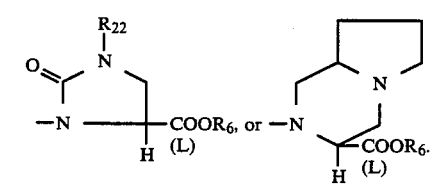

n is zero, one, or two.

$R_{22}$ is lower alkyl or 1 to 4 carbons

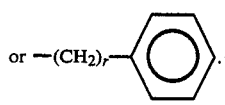

$R_7$ is hydrogen, lower alkyl, halogen, hydroxy,

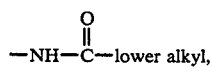

amino,

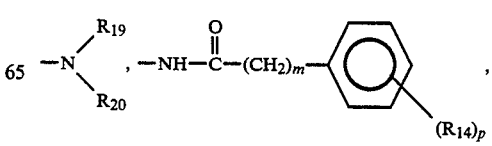

-continued

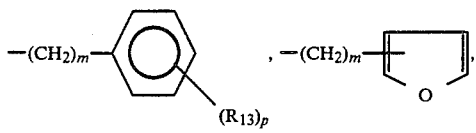 , 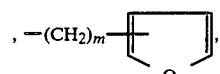 ,

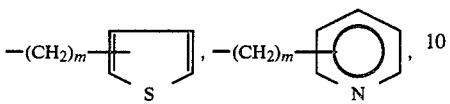 , a 1- or 2-naphthyl of the formula

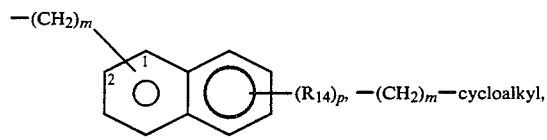, —(CH$_2$)$_m$—cycloalkyl,

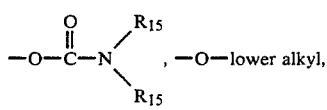, —O—lower alkyl,

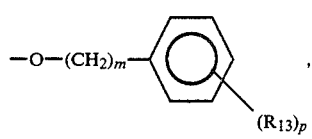 , a 1- or 2-naphthyloxy of the formula

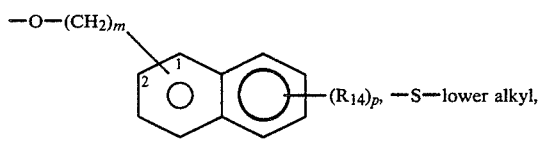,

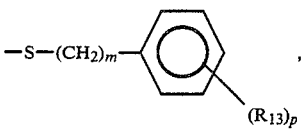 , or a 1- or 2-naphthylthio of the formula

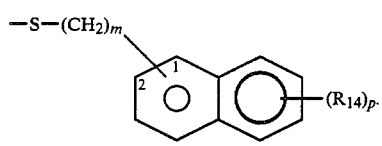

R$_8$ is halogen,

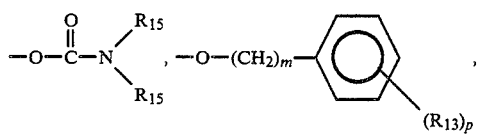,

—O—lower alkyl, a 1- or 2-naphthyloxy of the formula

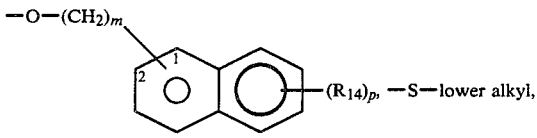

or a 1- or 2-naphthylthio of the formula

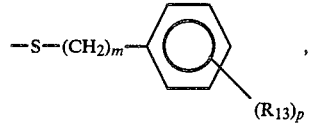

R$_9$ is keto or 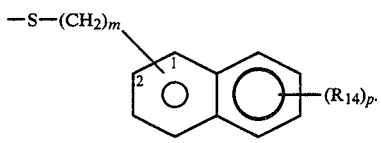

R$_{10}$ is halogen or —Y—R$_{16}$.

R$_{11}$, R'$_{11}$, R$_{12}$ and R'$_{12}$ are independently selected from hydrogen and lower alkyl or R'$_{11}$, R$_{12}$ and R'$_{12}$ are hydrogen and R$_{11}$ is

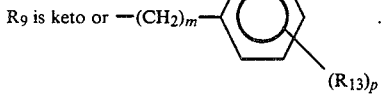

R$_{13}$ is hydrogen, lower alkyl of 1 to 4 carbons, lower alkoxy of 1 to 4 carbons, lower alkylthio of 1 to 4 carbons, chloro, bromo, fluoro, trifluoromethyl, hydroxy, phenyl, phenoxy, phenylthio, or phenylmethyl.

R$_{14}$ is hydrogen, lower alkyl of 1 to 4 carbons, lower alkoxy of 1 to 4 carbons, lower alkylthio of 1 to 4 carbons, chloro, bromo, fluoro, trifluoromethyl, or hydroxy.

m is zero, one, two, three, or four.

p is one, two or three provided that p is more than one only if R$_{13}$ or R$_{14}$ is hydrogen, methyl, methoxy, chloro, or fluoro.

R$_{15}$ is hydrogen or lower alkyl of 1 to 4 carbons.

Y is oxygen or sulfur.

R$_{16}$ is lower alkyl of 1 to 4 carbons,

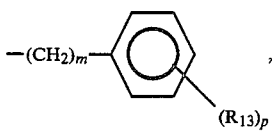

or the R$_{16}$ groups join to complete an unsubstituted 5- or 6-membered ring or said ring in which one or more of the carbons has a lower alkyl of 1 to 4 carbons or a di(lower alkyl of 1 to 4 carbons) substituent.

R$_4$ is hydrogen, lower alkyl,

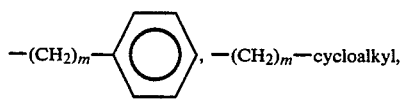

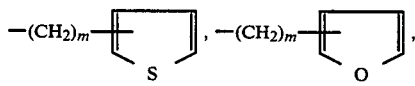

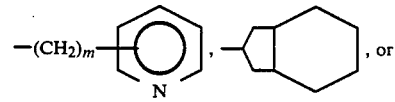

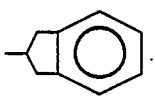

$R_5$ is hydrogen, lower alkyl,

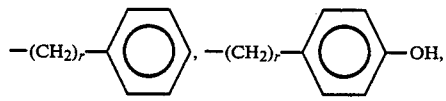

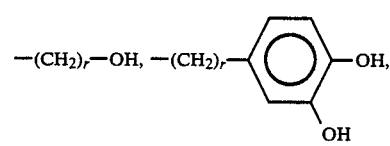

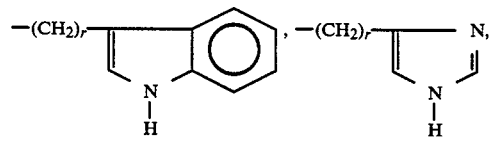

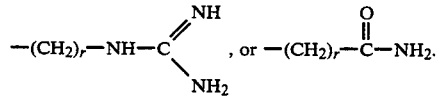

r is an integer from 1 to 4.
$R_{19}$ is lower alkyl, benzyl, or phenethyl.
$R_{20}$ is hydrogen, lower alkyl, benzyl or phenethyl.
$R_1$ is hydrogen, lower alkyl, halo substituted lower alkyl,

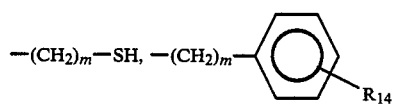

—(CH$_2$)$_m$—OH, —(CH$_2$)$_m$—NH$_2$, or —(CH$_2$)$_m$—cycloalkyl.
$R_3$ is lower alkyl,

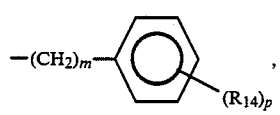

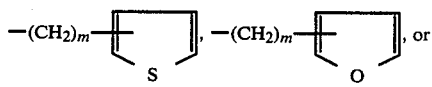

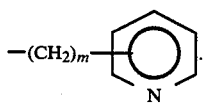

$R_2$ and $R_6$ are independently selected from hydrogen, lower alkyl, benzyl, benzhydryl, and

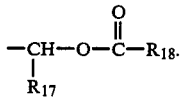

$R_{17}$ is hydrogen, lower alkyl, cycloalkyl, or phenyl.
$R_{18}$ is hydrogen, lower alkyl, lower alkoxy, or phenyl.
$R_{21}$ is hydrogen, lower alkyl,

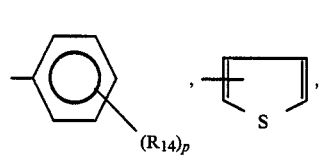

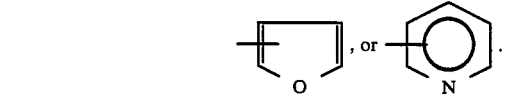

DETAILED DESCRIPTION OF THE INVENTION

This invention in its broadest aspects relates to the N-acyl-γ-glutamyl imino and amino acids and esters of formula I above, to compositions and the method of using such compounds as pharmaceutical agents.

The term lower alkyl used in defining various symbols refers to straight or branched chain radicals having up to seven carbons. The preferred lower alkyl groups are up to four carbons with methyl and ethyl most preferred. Similarly the terms lower alkoxy and lower alkylthio refer to such lower alkyl group attached to an oxygen or sulfur.

The term cycloalkyl refers to saturated rings of 4 to 7 carbon atoms with cyclopentyl and cyclohexyl being most preferred.

The term halogen refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The symbols

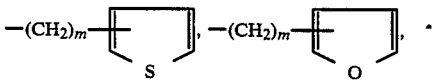

and

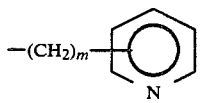

represent that the alkylene bridge is attached to an available carbon atom.

The compounds of formula I can be prepared by various methods. For example, an N-protected glutamic acid, monoester of the formula

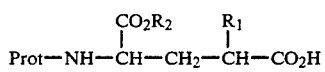   (II)

wherein Prot is a protecting group such as benzyloxycarbonyl or t-butoxycarbonyl and $R_2$ is an ester group such as lower alkyl, benzyl, or benzhydryl is coupled with an imino or amino acid or ester of the formula

HX   (III)

to give

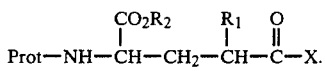   (IV)

Preferably, the coupling reaction is performed in the presence of a coupling agent such as dicyclohexylcarbodiimide and $R_6$ in the definition of X is an ester group such as lower alkyl, benzyl, or benzhydryl. Alternatively, the glutamic acid, monoester of formula II can be converted to the acid chloride by treatment with thionyl chloride or oxalyl chloride and this acid chloride can be coupled with the imino or amino acid of formula III in the presence of base such as sodium bicarbonate.

The intermediate of formula IV is treated to remove the N-protecting group, for example, with trifluoroacetic acid when Prot is t-butoxycarbonyl or hydrogenated in the presence of palladium/carbon catalyst when Prot is benzyloxycarbonyl, followed by acylation with the acid chloride

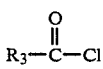   (V)

in the presense of base such as sodium bicarbonate to give the compound of formula I.

The compounds of formula I wherein either or both of $R_2$ and $R_6$ are lower alkyl, benzyl, or benzhydryl can be hydrogenated, for example by treating with hydrogen in the presence of palladium/carbon catalyst or chemically treated with sodium hydroxide to yield the compounds of formula I wherein $R_2$ and $R_6$ are hydrogen.

In the above reactions if either $R_1$ or $R_5$ or both are

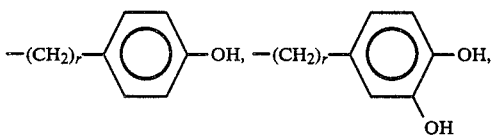

—$(CH_2)_r$—$NH_2$, —$(CH_2)_m$—$NH_2$, —$(CH_2)_r$—$SH$, —$(CH_2)_m$—$SH$, —$(CH_2)_r$—$OH$, —$(CH_2)_m$—$OH$,

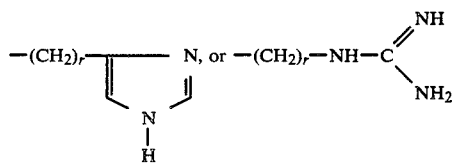

then the hydroxyl, amino, imidazolyl, mercaptan, or quanidinyl function should be protected during the reaction. Suitable protecting groups include benzyloxycarbonyl, t-butoxycarbonyl, benzyl, benzhydryl, trityl, etc., and nitro in the case of guanidinyl. The protecting group is removed by hydrogenation, treatment with acid, or by other known means following completion of the reaction.

The ester products of formula I wherein $R_6$ is

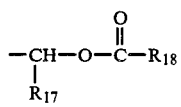

may be obtained by employing the imino or amino acid of formula III in the above reactions with the ester group already in place. Such ester reactants can be prepared by treating the imino or amino acid with an acid chloride such as

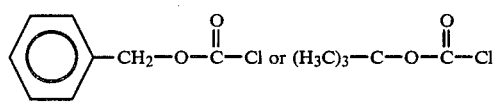

so as to protect the N-atom. The protected compound is then reacted in the presence of a base with a compound of formula

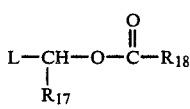   (VI)

wherein L is a leaving group such as chlorine, bromine, tolylsulfonyl, etc., followed by removal of the N-protecting group such as by treatment with acid or hydrogenation.

The ester products of formula I wherein $R_6$

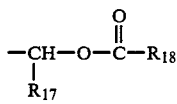

can also be obtained by treating the product of formula I wherein $R_6$ is hydrogen with a molar equivalent of the compound of formula VI. The diester products wherein $R_2$ and $R_6$ are the same and are

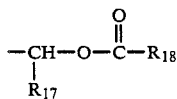

can be obtained by treating the product of formula I wherein $R_2$ and $R_6$ are both hydrogen or an alkali metal salt with two or more equivalents of the compound of formula VI.

The ester products of formula I wherein $R_2$ is

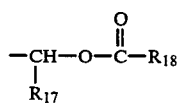

can be obtained by treating the product of formula I wherein $R_2$ is hydrogen or an alkali metal salt and $R_6$ is benzyl or benzhydryl with the compound of formula VI in the presence of base. Removal of the $R_6$ ester group such as by hydrogenation yields the products of formula I wherein $R_2$ is

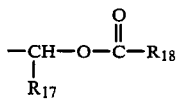

and $R_6$ is hydrogen.

The products of formula I wherein $R_7$ is amino may be obtained by reducing the corresponding products of formula I wherein $R_7$ is azido.

Methods of preparing the N-protected glutamic acid, monoesters of formula II are reported in the literature as note, for example, Pietta et al., J. Organic Chem., Vol. 36, p. 3966-3970 (1971). When the glutamic acid compound is known, it can be treated so as to introduce the N-protecting group and then the monoester group. For example, treatment of N-benzyloxycarbonyl glutamic acid with methyl iodide or dimethylsulfate in the presence of triethylamine gives the desired monomethyl ester starting material.

Similarly, the imino and amino acid esters of formula III are known or can be readily obtained by converting the acid to the ester by conventional means.

Preferred compounds of this invention with respect to the imino or amino acid or ester part of the structure of formula I are those wherein:

$R_4$ is hydrogen, cyclohexyl or phenyl.

$R_5$ is hydrogen, straight or branched chain lower alkyl of 1 to 4 carbons, —$CH_2OH$,

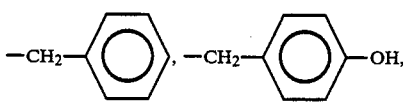

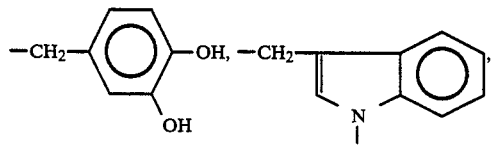

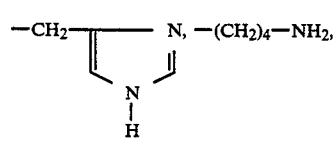

—$CH_2$—SH, —$(CH_2)_2$—S—$CH_3$,

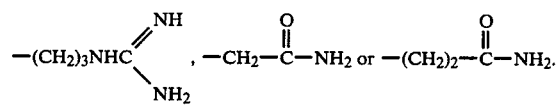

$R_6$ is hydrogen, straight or branched chain lower alkyl of 1 to 4 carbons, alkali metal salt ion, or

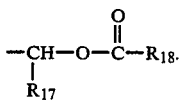

$R_{17}$ l is hydrogen, straight or branched chain lower alkyl of 1 to 4 carbons, or cyclohexyl.

$R_{18}$ is straight or branched chain lower alkyl of 1 to 4 carbons or phenyl.

$R_7$ is hydrogen.

$R_7$ is hydroxy.

$R_7$ is straight or branched chain lower alkyl of 1 to 4 carbons or cyclohexyl.

$R_7$ is amino.

$R_7$ is —O-lower alkyl wherein lower alkyl is straight or branched chain of 1 to 4 carbons.

$R_7$ is

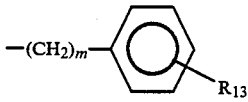

wherein m is zero, one or two and $R_{13}$ is hydrogen, methyl, methoxy, methylthio, chloro, bromo, fluoro, or hydroxy.

$R_7$ is

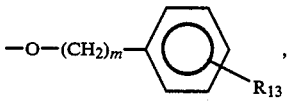

1-naphthyloxy or 2-naphthyloxy wherein m is zero, one, or two and $R_{13}$ is hydrogen, methyl, methoxy, methylthio, chloro, bromo, fluoro, or hydroxy.

$R_7$ is —S-lower alkyl wherein lower alkyl is straight or branched chain of 1 to 4 carbons.

$R_7$ is

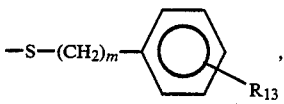

1-naphthylthio, or 2-naphthylthio wherein m is zero, one, or two and $R_{13}$ is hydrogen, methyl, methoxy, methylthio, chloro, bromo, fluoro or hydroxy.

$R_8$ is —O-lower alkyl wherein lower alkyl is straight or branched chain of 1 to 4 carbons.

$R_8$ is

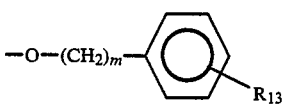

wherein m is zero, one, or two and $R_{13}$ is hydrogen, methyl, methoxy, methylthio, chloro, bromo, fluoro, or hydroxy.

$R_8$ is —S-lower alkyl wherein lower alkyl is straight or branched chain of 1 to 4 carbons.

$R_8$ is

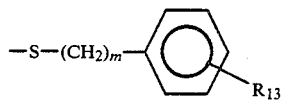

wherein m is zero, one or two and $R_{13}$ is hydrogen, methyl, methoxy, methylthio, chloro, bromo, fluoro or hydroxy.

$R_9$ is phenyl, 2-hydroxyphenyl, or 4-hydroxyphenyl.

$R_{10}$ are both fluoro or chloro.

$R_{10}$ are both —Y-$R_{16}$ wherein Y is O or S, $R_{16}$ is straight or branched chain lower alkyl of 1 to 4 carbons or the $R_{16}$ groups join to complete an unsubstituted 5- or 6-membered ring or said ring in which one or more of the available carbons has a methyl or dimethyl substituent.

$R_{11}$, $R'_{11}$, $R_{12}$ and $R'_{12}$ are all hydrogen, or $R_{11}$ is phenyl, 2-hydroxyphenyl, or 4-hydroxyphenyl and $R'_{11}$, $R_{12}$ and $R'_{12}$ are hydrogen.

$R_{21}$ is phenyl.

Most preferred compounds of this invention with respect to the imino or amino acid or ester part of the structure of formula I are those wherein:

X is

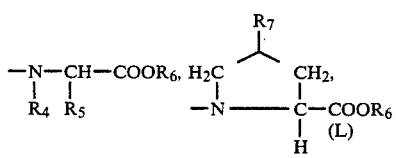

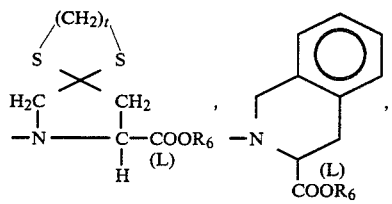

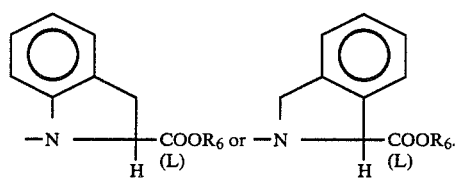

$R_6$ is hydrogen or an alkali metal salt ion.
$R_4$ is cyclohexyl or phenyl and $R_5$ is hydrogen.
$R_4$ is hydrogen and $R_5$ is methyl, —$CH_2$-$CH(CH_3)_2$,

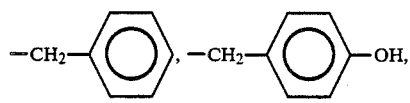

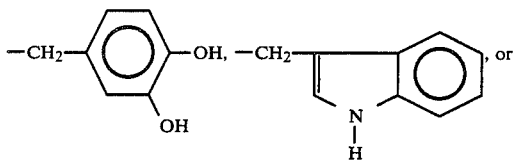

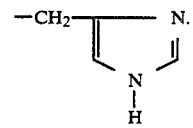

$R_7$ is hydrogen, cyclohexyl, lower alkoxy of 1 to 4 carbons,

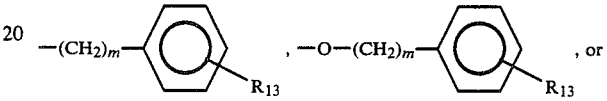

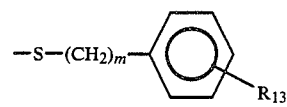

wherein m is zero, one, or two and $R_{13}$ is hydrogen, methyl, methoxy, methylthio, Cl, Br, F, or hydroxy, especially preferred wherein $R_7$ is hydrogen.

t is two or three, especially where t is two.

Preferred compounds of this invention with respect to N-acyl-γ-glutamyl portion of the structure of formula I are those wherein:

$R_1$ is hydrogen, straight or branched chain lower alkyl of 1 to 4 carbons, or benzyl, especially wherein $R_1$ is hydrogen.

$R_2$ is hydrogen, straight or branched chain lower alkyl of 1 to 4 carbons, alkali metal salt ion, or

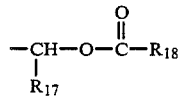

wherein $R_{17}$ is hydrogen, straight or branched chain lower alkyl of 1 to 4 carbons, or cyclohexyl and $R_{18}$ is straight or branched chain lower alkyl of 1 to 4 carbons or phenyl, especially wherein $R_2$ is hydrogen or alkali metal salt ion.

$R_3$ is

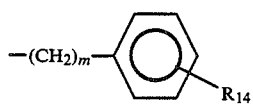

wherein m is zero, one or two and $R_{14}$ is hydrogen, methyl, methoxy, methylthio, chloro, bromo, fluoro, or hydroxy, especially wherein $R_3$ is phenyl.

The compounds of formula I wherein $R_2$ or $R_6$ or both are hydrogen form salts with a variety of inorganic or organic bases. The non-toxic, pharmaceutically acceptable salts are preferred, although other salts are also useful in isolation or purifying the product. Such pharmaceutically acceptable salts include metal salts such as sodium, potassium or lithium, alkaline earth metal salts such as calcium or magnesium, and salts derived from amino acids such as arginine, lysine, etc. The salts are obtained by reacting the acid form of the compound with an equivalent of the base supplying the desired ion in a medium in which the salt precipitates or in aqueous medium and then lyophilizing.

Also, the compounds of formula I containing a free amino function form salts with a variety of inorganic and organic acids. Again, the non-toxic pharmaceutically acceptable salts are preferred, although other salts are also useful in isolating or purifying the product. Such pharmaceutically acceptable salts include those formed with hydrochloric acid, methanesulfonic acid, sulfuric acid, maleic acid, etc. The salts are obtained by reacting the product with an equivalent amount of the acid in a medium in which the salt precipitates.

The compounds of formula I contain one or two asymmetric centers (one center when $R_1$ is hydrogen) in the N-acyl-γ-glutamyl sidechain. Thus, the compounds of formula I can exist in diastereoisomeric forms or in mixtures thereof. The above described processes can utilize racemates, enantiomers or diastereomers as starting materials. When diastereomeric products are prepared, they can be separated by conventional chromatographic or fractional crystallization methods. The asymmetric center identified with the * in formula I is preferably in the R-configuration, i.e., D-glutamyl.

The products of formula I wherein the imino acid ring is monosubstituted also give rise to cis-trans isomerism. The configuration of the final product will depend upon the configuration of the $R_7$, $R_8$ and $R_9$ substituent in the starting material of formula III.

The compounds of formula I, and the pharmaceutically acceptable salts thereof, are hypotensive agents. They inhibit the conversion of the decapeptide angiotensin I to angiotensin II and, therefore, are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the causative agent in several forms of hypertension in various mammalian species, e.g., humans. The compounds of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one (or a combination) of the compounds of this invention, angiotensin dependent hypertension in a species of mammal (e.g., humans) suffering therefrom is alleviated. A single dose, or preferably two or four divided daily doses, provided on a basis of about 0.1 to 100 mg., preferably about 1 to 50 mg. per kg. of body weight per day is appropriate to reduce blood pressure. The substance is preferably administered orally, but parenteral routes such as the subcutaneous, intramuscular, intravenous or intraperitoneal routes can also be employed.

The compounds of this invention can also be formulated in combination with a diuretic for the treatment of hypertension. A combination product comprising a compound of this invention and a diuretic can be administered in an effective amount which comprises a total daily dosage of about 30 to 600 mg., preferably about 30 to 330 mg. of a compound of this invention, and about 15 to 300 mg., preferably about 15 to 200 mg. of the diuretic, to a mammalian species in need thereof. Exemplary of the diuretics contemplated for use in combination with a compound of this invention are the thiazide diuretics, e.g., chlorothiazide, hydrochlorothiazide, flumethiazide, hydroflumethiazide, bendroflumethiazide, methyclothiazide, trichloromethiazide, polythiazide or benzthiazide as well as ethacrynic acid, ticrynafen, chlorthalidone, furosemide, musolimine, bumetanide, triamterene, amiloride and spironolactone and salts of such compounds.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The compounds of formula I wherein X is

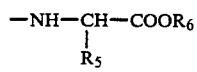

also possess enkephalinase inhibition activity and are useful as analgesic agents. Thus, by the administration of a composition containing one or a combination of such compounds of formula I or a pharmaceutically acceptable salt thereof, pain is alleviated in the mammalian host. A single dose, or preferably two to four divided daily doses, provided on a basis of about 0.1 to about 100 mg. per kilogram of body weight per day, preferably about 1 to about 50 mg. per kilogram per day, produces the desired analgesic activity. The composition is preferably administered orally but parenteral routes such as subcutaneous can also be employed.

The following examples are illustrative of the invention. Temperatures are given in degrees centigrade. LH-20 refers to a Sephadex chromatography gel commercially available from Pharmacia Fine Chemicals.

EXAMPLE 1

1-(N-Benzoyl-L-γ-glutamyl)-L-proline (a) 
1-[(S)-4-[[(1,1-Dimethylethoxy)carbony]amino]-1,5-dioxo-5-(phenylmethoxy)pentyl]-L-proline, 1,1-dimethylethyl ester N-[(1,1-Dimethylethoxy)carbonyl]-L-glutamic acid, 1-(phenylmethyl)ester (3.37 g.) and L-proline, 1,1-dimethylethyl ester (1.77 g.) are dissolved in 50 ml. of dichloromethane with stirring in an ice bath. Dicyclohexylcarbodiimide (2.06 g.) is added and after 15 minutes the mixture is removed from the ice bath and stirred overnight at room temperature. Dicyclohexylurea is filtered off and the filtrate is concentrated to dryness in vacuo. The residue is taken into ethyl acetate and washed with 5% potassium bisulfate, water, saturated sodium bicarbonate, water, dried (MgSO$_4$), and taken to dryness in vacuo. The crude material (5 g.) is taken into chloroform and applied to a silica gel column (150 g.) packed in chloroform. The product (3.7 g.) is eluted with chloroform. It is then triturated with ether-hexane to give 3.12 g. of 1-[(S)-4-[[(1,1-dimethylethoxy)carbonyl]amino]-1,5-dioxo-5-(phenylmethoxy)pentyl]-L-proline, 1,1-dimethylethyl ester; m.p. (104°) 105°–106°.

Anal.calc'd. for $C_{26}H_{38}O_7N_2$: C, 63.81; H, 6.43; N, 5.96 Found: C, 63.54; H, 6.71, N, 5.85.

(b) 1-(L-4-Amino-4-carboxy-1-oxobutyl)-L-proline

The ester product from part (a) (approximately 3 g.) is dissolved in 30 ml. of trifluoroacetic acid and stored for one hour at room temperature. It is concentrated to dryness in vacuo and precipitated twice from ether-hexane to remove excess trifluoroacetic acid and give 2.3 g. of 1-[L-4-amino-4-[(phenylmethoxy)carbonyl]-1-oxobutyl]-L-proline.

This residue (2.3 g.) is dissolved in 30 ml. of methanol and 10 ml. of water are added. This mixture is stirred overnight under positive hydrogen pressure with 300 mg. of 10% palladium/carbon catalyst, filtered, and concentrated to dryness in vacuo. The residue is crystallized from acetonitrile to give 1.06 g. of 1-(L-4-amino-4-carboxy-1-oxobutyl-L-proline; m.p. (208°) 210°.

Anal. calc'd. for $C_{10}H_{16}O_2N_5$: C, ;b 49.17; H, 6.60; N, 11.47 Found: C, 48.92; H, 6.55; N, 11.22.

(c) 1-(N-Benzoyl-L-γ-glutamyl)-L-proline 1-(L-4-Amino-4-carboxy-1-oxobutyl)-L-proline (260 mg., 1.06 mmole) is dissolved in 10 ml. of saturated aqueous sodium bicarbonate. Benzoyl chloride (0.148 ml., 1.27 mmole) is added with rapid stirring followed by 1 ml. of tetrahydrofuran. After stirring for three hours the mixture is adjusted to pH 2.0 with 6N hydrochloric acid, saturated with sodium chloride, and extracted several times with ethyl acetate. The ethyl acetate layers are combined, dried ($Na_2SO_4$), and stripped. The residue is triturated to a white solid with ethyl ether, filtered, and dried to give 250 mg. of hydroscopic 1-(N-benzoyl-L-γ-glutamyl)-L-proline; m.p. 102°–104°.

Anal. calc'd. for $C_{17}H_{20}N_2O_6.1.0H_2O$: C, 55.73; H, 6.05; N, 7.65 Found: C, 55.71; H, 5.64; N, 7.24.

EXAMPLE 2

1-(N-Benzoyl-D-γ-glutamyl)-L-proline (a)
1-[(R)-4-[[(1,1-Dimethylethoxy)carbonyl]amino]-1,5-dioxo-5-(phenylmethoxy)pentyl]-L-proline, 1,1-dimethylethyl ester A solution of N-[(1,1-dimethylethoxy)-carbonyl]-D-glutamic acid, 1-(phenylmethyl)ester (2.85 g., 8.45 mmole), L-proline, 1,1-dimethylethyl ester (1.45 g., 8.5 mmole), and hydroxybenzotriazole hydrate (1.15 g., 8.5 mmole) in dichloromethane (50 ml.) is cooled to 0° and dicyclohexylcarbodiimide (8.5 mmole) is added. The mixture is allowed to warm to ambient temperature and stirred overnight. The reaction is then filtered and stripped and the residue is redissolved in ethyl acetate. After filtration the solution is washed with aqueous potassium bisulfate and aqueous sodium bicarbonate, dried (MgSO$_4$), and stripped to give 4.17 g. of crude 1-[(R)-4-[[(1,1-dimethylethoxy)carbonyl]amino]-1,5-dioxo-5-(phenylmethoxy)pentyl]-L-proline, 1,1-dimethylethyl ester.

(b)
1-[(R)-4-[(Phenylcarbonyl)amino]-1,5-dioxo-5-(phenylmethoxy)pentyl]-L-proline The ester product from part (a) (4.17 g.) is dissolved in trifluoroacetic acid (50 ml.) and stirred for three hours at room temperature. After concentration and evacuation ($10^{-1}$ torr) for several hours, the crude residue is dissolved in sodium bicarbonate (100 ml.) and benzoyl chloride (1.40 g., 10 mmole) and tetrahydrofuran (10 ml.) are added. The mixture is then vigorously stirred for three hours and extracted with ethyl acetate. The aqueous phase is then adjusted to pH of one with concentrated hydrochloric acid and extracted with ethyl acetate. Drying and concentrating of the organic phases gives an oily residue which is chromatographed on LH-20 using methanol as the eluant. Concentration of the product containing fraction gives 1.95 g. of 1-[(R)-4-[(phenylcarbonyl)amino]-1,5-dioxo-5-(phenylmethoxy)pentyl]-L-proline as a pale yellow glass.

(c) 1-(N-Benzoyl-D-γ-glutamyl)-L-proline

The ester product from part (b) (1.95 g.) is dissolved in ethanol (100 ml.), treated with 10% palladium/carbon catalyst (0.3 g.), and stirred under an atmosphere of hydrogen for sixteen hours. The mixture is then filtered (Celite) and stripped to give a solid residue. This material is dissolved in a small amount of water and lyophilized to give 1.20 g. of white solid 1-(N-benzoyl-D-γ-glutamyl)-L-proline; m.p. 106°–108°.

Anal calc'd. for $C_{17}H_{20}N_2O_6.0.62H_2O$: C, 56.80; H, 5.95; N, 7.79 Found: C, 56.80; H, 5.80; N, 7.45.

EXAMPLE 3

(S)-1-(N-Benzoyl-γ-D-glutamyl)-2,3-dihydro-1H-indole-2-carboxylic acid (a) N-[(1,1-Dimethylethoxy)carbonyl]-D-glutamic acid Dioxane (200 ml.) and [(2-tert-butoxycarbonyloxyimino)-2-phenylacetonitrile] (1.1 eq., 0.22 mole, 54.18 g.) are added to a magnetically stirred solution of D-glutamic acid (1 eq., 0.2 mole, 30.0 g.) in water (200 ml.) and triethylamine (41.8 ml.). The mixture is allowed to stir overnight at room temperature. The solvent volume is reduced by about 50% in vacuo and the milky mixture is poured into ethyl acetate (150 ml.) and the layers are separated. The aqueous layer is washed with ethyl acetate (2×200 ml.) and the combined organic layers are discarded. The aqueous layer is adjusted to pH of two with a combination of solid citric acid and 5% aqueous potassium bisulfate. The acidified aqueous layer is salted and extracted with ethyl acetate (4×250 ml.). The combined organic layers are dried (MgSO$_4$), filtered, and the solvent removed in vacuo to yield N-[(1,1-dimethylethoxy)carbonyl]-D-glutamic acid as a clear, colorless oil.

(b) (R)-(Tetrahydro-2,6-dioxo-2H-pyran-3-yl)carbamic acid, dimethylethyl ester

A solution of dicyclohexylcarbodiimide (1.1 eq., 32 mmole, 6.6 g.) in 30 ml. of dry tetrahydrofuran is added dropwise to a solution of N-[(1,1-dimethylethoxy)carbonyl]-D-glutamic acid (1 eq., 29 mmole, 7.16 g.) in 30 ml. of dry tetrahydrofuran at 0° under a nitrogen atmosphere. The mixture is stirred at 0° for three hours and stored overnight in the freezer. The mixture is filtered to remove dicyclohexyurea and the filtrate is concentrated in vacuo to yield a green gum. This gum is triturated in hexane/acetone to yield 4.32 g. of (R)-(tetrahydro-2,6-dioxo-2H-pyran-3-yl)carbamic acid, dimethylethyl ester as a white solid; m.p. 117°–119°.

(c) N-[(1,1-Dimethylethoxy)carbonyl]-D-glutamic acid, 1-(phenylmethyl)ester

A mixture of the ester product from part (b) (1 eq., 18.9 mmole, 4.32 g.) and benzyl alcohol (3 eq., 56.7 mmole, 5.9 ml., freshly distilled) in 10 ml. of dry tetrahydrofuran at room temperature under nitrogen is treated dropwise with a solution of dicyclohexylamine (1.1 eq., 20.8 mmole, 4.1 ml.) in 100 ml. of anhydrous ether. A white solid forms, and the thick suspension is mechanically stirred overnight. The solid is collected by filtration and washed with ether to yield the dicyclohexylamine salt as a gummy solid. The solid is dried at 40° under vacuum for one day. The solid is taken into 5% potassium bisulfate and extracted with ethyl acetate (4×100 ml.). The combined ethyl acetate layers are dried (MgSO$_4$), filtered and the solvent stripped in vacuo to yield N-[(1,1-dimethylethoxy)-carbonyl]-D-glutamic acid, 1-(phenylmethyl)ester; m.p. 91°–94°.

(d) (S)-2,3-Dihydro-1H-indole-2-carboxylic acid, ethyl ester

A suspension of N-acetyl-(S)-2,3-dihydro-1H-indole-2-carboxylic acid in 100 ml. of degassed 2N hydrochloric acid is degassed for 15 minutes under anhydrous nitrogen. The suspension is refluxed for 5 hours by which time all solids are in solution. The clear orange solution is cooled to room temperature and the hydrochloric acid is stripped in vacuo. The residue is recrystallized from isopropyl alcohol and ether to yield 11.13 g. of (S)-2,3-dihydro-1H-indole-2-carboxylic acid, hydrochloride as beige crystalline solid; m.p. 165°–170°.

A mixture of this material (2.0 g.) in 20 ml. of ethanol saturated with hydrochloric acid gas is allowed to stir at room temperature for 2 hours. The ethanol is stripped in vacuo until crystallization begins and then the solids are allowed to crystallize out in the freezer (0°) for 2 days. The crystals are collected by filtration to yield 2.0 g. of (S)-2,3-dihydro-1H-indole-2-carboxylic acid, ethyl ester as a beige solid; m.p. 178°–179°; $[\alpha]_D = -63.2°$ (c=1, ethanol).

(e) (S)-1-[(R)-4-[[(1,1-Dimethylethoxy)carbonyl]-amino]-1,5-dioxo-5-(phenylmethoxy)pentyl]-2,3-dihydro-1H-indole-2-carboxylic acid, ethyl ester A mixture of N[(1,1-dimethylethoxy)-carbonyl]-D-glutamic acid, 1-(phenylmethyl) ester (1 eq., 6.5 mmole, 2.21 g.), hydroxybenzotriazole hydrate (1.2 eq., 7.8 mmole, 1.05 g.) and dicyclohexylcarbodiimide (1.2 eq., 7.8 mmole, 1.61 g.) in 13 ml. of dimethylformamide at 0° under nitrogen is allowed to stir for one hour. (S)-2,3-Dihydro-1H-indole-2-carboxylic acid, ethyl ester (1 eq., 6.5 mmole, 1.48 g.) and triethylamine (1 eq., 6.5 mmole, 0.91 ml.) are added to the mixture of 0°. The mixture is stirred for 3 days at room temperature, filtered to remove dicyclohexylurea, and the dimethylformamide is stripped in vauo. The residue is dissolved in ethyl acetate ane washed with saturated aqueous sodium bicarbonate, 1N hydrochloric acid, and brine. The ethyl acetate layers are dried (MgSO$_4$), filtered, and the solvent removed in vacuo to yield an oily residue. This residue is flash chromatographed on 300 g. LPS-1 eluting with (2:1) hexane:ethyl acetate. The residue from the column is triturated with cold ether to yield 0.44 g. of (S)-1-[(R)-4-[[(1,1-dimethylethoxy)carbonyl]amino]-1,5-dioxo-5-(phenylmethoxy)pentyl]-2,3-dihydro-1H-indole-2-carboxylic acid, ethyl ester.

(f) (S)-1-[(R)-4-[(Phenylcarbonyl)amino]-1,5-dioxo-5-(phenylmethoxy)pentyl]-2,3-dihydro-1H-indole-2-carboxylic acid, ethyl ester A mixture of the ester product from part (e) (0.39 mmole, 0.2 g.), anisole (0.2 ml.) and trifluoroacetic acid (1.95 ml.) is allowed to stir at room temperature for two hours. The trifluoroacetic acid is stripped in vacuo to yield (S)-1-[(R)-4-amino-1,5-dioxo-5-(phenylmethyl)-pentyl]-2,3-dihydro-1H-indole-2-carboxylic acid, ethyl ester, trifluoroacetate salt as a yellow oil.

A small amount of water, 1N sodium bicarbonate, and the above trifluoroacetate salt (1 eq., 0.38 mmole, 0.2 g.) are stirred together at room temperature while the pH is adjusted to 6.5 by the addition of aqueous sodium bicarbonate. Benzoyl chloride (1 eq., 0.38 mmole, 0.04 ml.) is added to the white slurry. The pH is maintained at 6.5 using aqueous 1N hydrochloric acid or aqueous 1N sodium bicarbonate as required. After 30 minutes, the pH stabilizes at 6.5 and the mixture is allowed to stir for 30 minutes more. Ethyl acetate is added to the mixture and the layers are separated. The aqueous layer is salted and extracted with ethyl acetate (2×50 ml.), the combined ethyl acetate layers are washed with saturated aqueous sodium bicarbonate, brine, dried (MgSO$_4$), filtered, and stripped in vacuo to yield the product as a white solid; m.p. 171°–172°. This solid is recrystallized from ethyl acetate/hexane to yield 0.1497 g. of (S)-1-[(R)-4-[(phenylcarbonyl)amino]-1,5-dioxo-5-(phenylmethoxy)pentyl]-2,3-dihydro-1H-indole-2-carboxylic acid, ethyl ester as white crystals; m.p. 172°–173°.

(g) (S)-1-(N-Benzoyl-γ-D-glutamyl)-2,3-dihydro-1H-indole-2-carboxylic acid

The ester product from part (f) (1 eq., 0.35 mmole, 0.22 g.) is suspended in 2.46 ml. of 1N sodium hydroxide and 20 ml. of tetrahydrofuran. Methanol is added until the solution is homogeneous. The mixture is stirred at room temperature for two hours, poured into ethyl acetate, and the layers are separated. The aqueous layer is washed with ethyl acetate (2×5 ml.) and then adjusted to a pH of two with concentrated hydrochloric acid. The resulting white crystalline solid is collected by filtration and washed with cold water. The solid is dried over phosphorus pentoxide under vacuum for three days to yield 0.12 g. of (S)-1-(N-benzoyl-γ-D-glutamyl)-2,3-dihydro-1H-indole-2-carboxylic acid; m.p. 162°–163°.

Anal. calc'd. for $C_{21}H_{20}N_2O_6 \cdot 0.75\, H_2O$: C, 61.56; H, 5.29; N, 6.84 Found: C, 61.59; H, 4.93; N, 6.75.

EXAMPLES 4–42

Following the procedures of Examples 1 to 3, the N-protected glutamic acid, monoester shown in Col. I is coupled with the imino or amino acid ester shown in Col. II to yield the intermediate shown in Col. III. Removal of the N-protecting group and acylation with the acid chloride shown in Col. IV yields the ester product shown in Col. V. Removal of the ester groups yields the acid product wherein $R_2$ and $R_6$ are both hydrogen. In the case of Examples 40 to 42 only the $R_2$ ester group would be removed.

Col. I

-continued

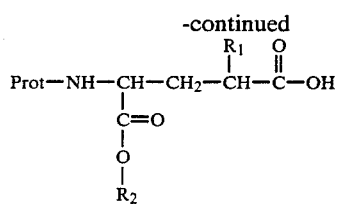

Col. II
HX

Col. III

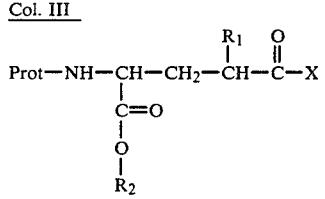

-continued

Col. IV

Col. V

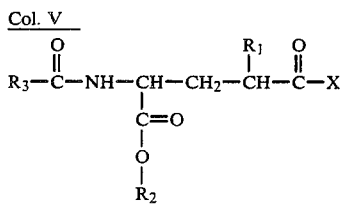

| Example | R₃ | R₂ | R₁ | X |
|---|---|---|---|---|
| 4 | phenyl- | -CH₂-phenyl | -CH₃ | -N(pyrrolidine)-COOC(CH₃)₃ (L) |
| 5 | 2-thienyl | -CH₂-phenyl | -H | -N-CH(CH₂-CH(SPh)-CH₂)-COOC(CH₃)₃ (L) |
| 6 | 2-furyl | -CH₂-phenyl | -H | -N-CH(CH₂-C(S)(S)-CH₂)-COOC(CH₃)₃ (L) |
| 7 | 3-pyridyl-CH₂- | -CH₂-phenyl | -C₂H₅ | -N-CH(CH₂-CH(Ph)-CH₂)-COOC(CH₃)₃ (L) |
| 8 | phenyl-CH₂- | -CH₂-phenyl | -H | -N-CH(CH₂-CH(cyclohexyl)-CH₂)-COOC(CH₃)₃ (L) |
| 9 | H₃C-C₆H₄- | -CH₂-phenyl | -CF₃ | -N-CH(CH₂-C(O)(O)-CH₂)-COOC(CH₃)₃ (L) |

4,568,489

-continued

| Example | R₃ | R₂ | R₁ | X |
|---|---|---|---|---|
| 10 | 4-Cl-C₆H₄-CH₂- | -CH₂-C₆H₅ | -CH₂-C₆H₅ | pyrrolidine-2-COOC(CH₃)₃ (L) |
| 11 | H₃C- | -CH₂-C₆H₅ | -CH₂-C₆H₄-F | 4-phenoxy-pyrrolidine-2-COOC(CH₃)₃ (L) |
| 12 | H₅C₂- | -CH₂-C₆H₅ | -C₆H₅ | 4-benzyl-pyrrolidine-2-COOC(CH₃)₃ (L) |
| 13 | H₇C₃- | -CH₂-C₆H₅ | -CH₂-C₆H₁₁ | 4,4-dichloro-pyrrolidine-2-COOC(CH₃)₃ (L) |
| 14 | C₆H₅- | -CH₂-C₆H₅ | -CH₂-C₅H₉ | 4-fluoro-pyrrolidine-2-COOC(CH₃)₃ (L) |
| 15 | C₆H₅- | -CH(C₆H₅)₂ | -H | 4-methyl-pyrrolidine-2-COOC(CH₃)₃ (L) |
| 16 | C₆H₅- | -C₂H₅ | -H | 4-(SCH₃)-pyrrolidine-2-COOC(CH₃)₃ (L) |
| 17 | C₆H₅- | -CH₂-C₆H₅ | -CH₃ | 4-azido-pyrrolidine-2-COOC(CH₃)₃ (L) |
| 18 | C₆H₅-(CH₂)₄- | -CH₂-C₆H₅ | -(CH₂)₄-NH-C(O)-CH₂-C₆H₅ | 1,2,3,4-tetrahydroisoquinoline-3-COOC(CH₃)₃ (L) |

-continued

| Example | R₃ | R₂ | R₁ | X |
|---|---|---|---|---|
| 19 | phenyl | $-CH_2-$phenyl | $-CH_2-S-CH_2-$phenyl | pyridine-CH$_2$-CH(NH-)COOC(CH$_3$)$_3$ (L) |
| 20 | phenyl-(CH$_2$)$_3-$ | $-CH_2-$phenyl | $-(CH_2)_2-O-CH_2-$phenyl | $-$N(H)$-$CH(COOC(CH$_3$)$_3$)$-$CH$_2$CH$_2$$-$S$-$CH$_2-$phenyl (L) |
| 21 | phenyl | $-CH_2-$phenyl | $-CH_2-NH-C(=O)-CH_2-$phenyl | phenyl-CH(-N(H)-)-(CH$_2$)$_3$-CH(COOC(CH$_3$)$_3$) (L) |
| 22 | phenyl | $-CH_2-$phenyl | $-CH_3$ | thiomorpholine-CH(COOC(CH$_3$)$_3$) (L) |
| 23 | phenyl | $-CH_2-$phenyl | $-H$ | piperidine-2-COOC(CH$_3$)$_3$ (L) |
| 24 | phenyl | $-CH_2-$phenyl | $-H$ | phenyl-C(=N-N(H)-)-CH$_2$-CH(COOC(CH$_3$)$_3$) (L) |
| 25 | phenyl | $-CH(-$phenyl$)_2$ | $-H$ | cyclohexane-1-CH$_2$-N(H)-, 2-CH(COOC(CH$_3$)$_3$) (L) |
| 26 | thiophene-2-CH$_2-$ | $-CH_2-$phenyl | $-CH_3$ | cyclohexane-1-CH$_2$-CH(N(H)-)(COOC(CH$_3$)$_3$)... (L) |
| 27 | furan | $-CH_2-$phenyl | $-H$ | imidazolidin-2-one, N-CH$_3$, N'-CH(COOC(CH$_3$)$_3$) (L) |

-continued

| Example | R₃ | R₂ | R₁ | X |
|---|---|---|---|---|
| 28 | —C₆H₅ | —CH₂—C₆H₅ | —H | —N(C₆H₅)—CH₂—COOC(CH₃)₃ |
| 29 | —C₆H₅ | —CH₂—C₆H₅ | —CH₃ | —N(C₆H₁₁)—CH₂—COOC(CH₃)₃ |
| 30 | 4-pyridyl | —CH₂—C₆H₅ | —H | —N(CH₃)—CH₂—COOC(CH₃)₃ |
| 31 | —C₆H₅ | —CH₂—C₆H₅ | —H | —NH—CH(L)(CH₃)—COOC(CH₃)₃ |
| 32 | —C₆H₅ | —CH₂—C₆H₅ | —H | —NH—CH(L)(CH₂—C₆H₅)—COOC(CH₃)₃ |
| 33 | —C₆H₅ | —CH₂—C₆H₅ | —H | —NH—CH(L)(CH₂—S—CH₃)—COOC(CH₃)₃ |
| 34 | —C₆H₅ | —CH₂—C₆H₅ | —CH₃ | —NH—CH(L)(CH₂—C(O)—NH₂)—COOC(CH₃)₃ |
| 35 | —C₆H₅ | —CH₂—C₆H₅ | —H | —NH—CH(L)(CH₂-(3-indolyl))—COOC(CH₃)₃ |
| 36 | —C₆H₅ | —CH₂—C₆H₅ | —H | —NH—CH(L)(CH₂—C₆H₄—OCH(C₆H₅)₂)—COOC(CH₃)₃ |
| 37 | —C₆H₅ | —CH₂—C₆H₅ | —H | —NH—CH(L)(CH₂—imidazolyl-N—CH(C₆H₅)₂)—COOC(CH₃)₃ |
| 38 | —C₆H₅ | —CH₂—C₆H₅ | —H | —NH—CH(L)((CH₂)₃—NH—C(=NH)—NH—NO₂)—COOC(CH₃)₃ |
| 39 | —C₆H₅ | —CH₂—C₆H₅ | —H | —NH—CH₂—COOC(CH₃)₃ |

| Example | R₃ | R₂ | R₁ | X |
|---|---|---|---|---|
| 40 |  | —CH₂— | —H | 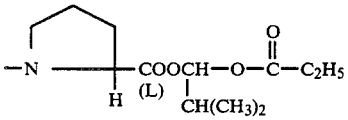 |
| 41 |  | —CH₂— | —H | 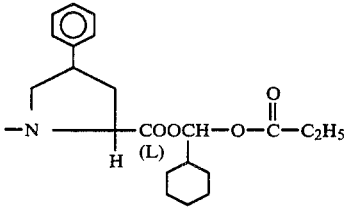 |
| 42 |  | —CH₂— | —CH₃ | 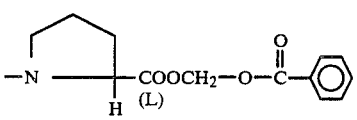 |

The $R_1$ protecting groups shown in Examples 18 to 21 and the $R_5$ protecting groups shown in Examples 36 to 38 are removed as the last step in the synthesis. The azidoproline of Example 17 when treated with a reducing agent yields a 4-aminoproline product.

EXAMPLE 43

1-(N-Benzoyl-D-γ-glutamyl)-L-proline disodium salt 1-(N-Benzoyl-D-γ-glutamyl)-L-proline (1 mmole) is dissolved in water (50 ml.). Aqueous sodium bicarbonate (0.1N, 20 ml.) is added and the aqueous solution is lyophilized. It is then dissolved in water (10 ml.) and applied on a column (5 cm. ×60 cm.) of a Sephadex chromatography gel G-10 and eluted with water. Fractions containing the desired product are pooled and lyophilized to give 1-(N-benzoyl-D-γ-glutamyl)-L-proline, disodium salt.

EXAMPLE 44

1000 tablets each containing the following ingredients:

| | |
|---|---|
| 1-(N—Benzoyl-D-Γ-glutamyl)-L-proline, disodium salt | 100 mg. |
| Corn starch | 50 mg. |
| Gelatin | 7.5 mg. |
| Avicel (microcrystalline cellulose) | 25 mg. |
| Magnesium stearate | 2.5 mg |
| | 185 mg. | are prepared from sufficient bulk quantities by mixing the 1-(N-benzoyl-D-γ-glutamyl)-L-proline, disodium salt and corn starch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 1 to 42 can be prepared.

A similar procedure can be employed to form tablets containing 50 mg. of active ingredient.

EXAMPLE 45

Two piece #1 gelatin capsules are filled with a mixture of the following ingredients:

| | |
|---|---|
| (S)—1-(N—Benzoyl-Γ-D-glutamyl)-2,3-dihydro-1H—indole-2-carboxylic acid, sodium salt | 50 mg. |
| Magnesium stearate | 7 mg. |
| Lactose | 193 mg. |
| | 250 mg. |

In a similar manner capsules containing 50 mg. of the product of any of Examples 1, 2 and 4 to 43 can be prepared.

EXAMPLE 46

A injectable solution is prepared as follows:

| | |
|---|---|
| 1-(N—Benzoyl-D-Γ-glutamyl)-L-proline, disodium salt | 500 g. |
| Methyl paraben | 5 g. |
| Propyl paraben | 1 g. |
| Sodium chloride | 25 g. |
| Water for injection | 5 l. |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any of Examples 1 to 42.

EXAMPLE 47

1000 tablets each containing the following ingredients:

| | |
|---|---|
| (S)-1-(N—Benzoyl-Γ-D-glutamyl)-2,3-dihydro-1H—indole-2-carboxylic acid, disodium salt | 100 mg. |
| Avicel | 100 mg. |
| Hydrochlorothiazide | 12.5 mg. |
| Lactose | 113 mg. |
| Cornstarch | 17.5 mg. |
| Stearic Acid | 7 mg. |
| | 350 mg. | are prepared from sufficient bulk quantities by slugging the (S)-1-(N-benzoyl-γ-D-glutamyl)-2,3-dihydro-1H-indole-2-carboxylic acid, disodium salt, Avicel, and a portion of the stearic acid. The slugs are ground and passed through a #2 screen, then mixed with the hydrochlorothiazide, lactose, cornstarch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 1, 2, and 4 to 43.

What is claimed is:

1. A compound of the formula $$R_3-\overset{O}{\underset{}{C}}-NH-\underset{COOR_2}{\overset{}{C}H}-CH_2-CH_2-\overset{O}{\underset{}{C}}-X$$

including a pharmaceutically acceptable salt thereof wherein:

X is

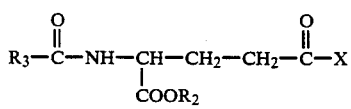, 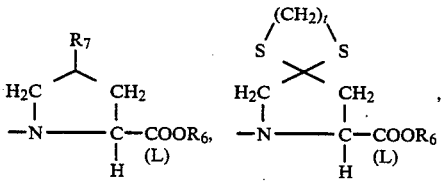,

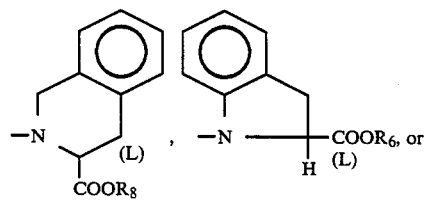,

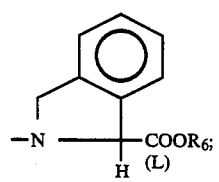

$R_2$ and $R_6$ are the same and both are hydrogen or an alkali metal salt ion;

$R_3$ is

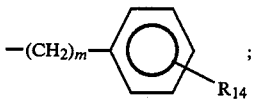;

$R_{14}$ is hydrogen, methyl, methoxy, methylthio, chloro, bromo, fluoro, or hydroxy;

$R_7$ is hydrogen, cyclohexyl, lower alkoxy of 1 to 4 carbons,

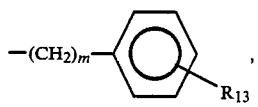,

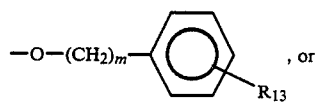, or

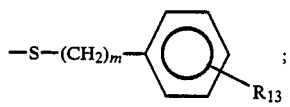;

m is zero, one or two;

$R_{13}$ is hydrogen, methyl, methoxy, methylthio, chloro, bromo, fluoro, or hydroxy; and t is 2 or 3.

2. A compound of claim 1 wherein:

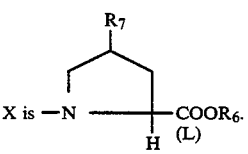

3. A compound of claim 2 wherein:
$R_7$ is hydrogen;
$R_3$ is phenyl;
$R_2$ is hydrogen, and
$R_6$ is hydrogen.

4. The compound of claim 3, 1-(N-benzoyl-D-γ-glutamyl)-L-proline.

5. A compound of claim 1 wherein:

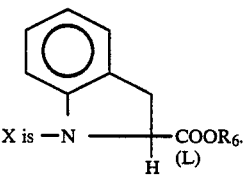

6. A compound of claim 5 wherein:
$R_3$ is phenyl;
$R_2$ is hydrogen; and
$R_6$ is hydrogen.

7. The compound of claim 6, (S)-1-(N-benzoyl-γ-D-glutamyl)-2,3-dihydro-1H-indole-2-carboxylic acid.

8. A compound of claim 1 wherein $R_3$ is phenyl.

* * * * *